US00PP07913P

United States Patent [19]

Giacomo

[11] Patent Number: Plant 7,913

[45] Date of Patent: Jul. 14, 1992

[54] *CHRYSANTHEMUM FRUTESCENS* PLANT NAMED CAMILLA PONTICELLI

[75] Inventor: Noli Giacomo, Camporosso, Italy

[73] Assignee: Istituto Regionale per la Floricoltura, San Remo, Italy

[21] Appl. No.: 604,226

[22] Filed: Oct. 29, 1990

[51] Int. Cl.[5] ..... A01H 5/00

[52] U.S. Cl. ..... Plt./74.1

[58] Field of Search ..... Plt./68, 74

*Primary Examiner*—James R. Feyrer

*Attorney, Agent, or Firm*—Foley & Lardner

[57] ABSTRACT

A new and unique cultivar of *Chrysanthemum frutescens* named 'Camilla Ponticelli' having white flower color with a gold-yellow disc, compact growth habit, dense branching, early natural season flowering, and the ability to be cultivated as a greenhouse or outdoor cultivar.

1 Drawing Sheet

The present invention comprises a new and distinct cultivar of Chrysanthemum, botanically known as *Dendranthema frutescens,* commercially known by the designation "daisy", and hereinafter referred to by the cultivar name 'Camilla Ponticelli'.

'Camilla Ponticelli' was originated by the inventor Noli Giacomo in a controlled breeding program in Sanremo, Italy in 1983. The new cultivar was produced from a self-pollination of the vegetatively propagated parent cultivar 'Italia'.

'Camilla Ponticelli' was discovered and selected as one flowering plant within the progeny of the stated self-pollination by the inventor in 1983 in a controlled environment in Sanremo, Italy.

The first act of asexual reproduction of 'Camilla Ponticelli' was accomplished when vegetative cuttings were taken from the initial selection in 1984 in a controlled environment in Sanremo, Italy by the inventor. Although viable seeds are produced, asexual propagation is the preferred form of propagation.

Horticultural examination of selected units initiated following propagation has demonstrated that the combination of characteristics as herein disclosed for 'Camilla Ponticelli' are firmly fixed and are retained through successive generations of asexual reproduction.

The new cultivar has not been observed under all possible environmental conditions. The phenotype may vary significantly with variations in environment such as temperature, light intensity and day length, without, however, any variation in genotype. The following observations, measurements and comparisons describe plants grown in Sanremo, Italy under greenhouse conditions which approximate those generally used in commercial greenhouse practice.

The following traits have been repeatedly observed and are determined to be basic characteristics of 'Camilla Ponticelli', which, in combination, distinguish this Chrysanthemum as a new and distinct cultivar:

1. A daisy pot capable of production under greenhouse of outdoor culture.
2. Compact growth habit, with numerous lateral shoots being formed which result in dense branching.
3. White ray floret color with golden yellow disc.
4. Grey-green foliage color.
5. Early natural season flowering in Sanremo, flowering in spring and through the summer.

The new cultivar is similar in several phenotypic respects to its parent, with the principal distinguishing features being the significantly more compact growth habit of 'Camilla Ponticelli', and its grey-green foliage, with 'Italia' having foliage which is more "spinach-green" in color. The new cultivar produces many more lateral shoots which result in dense branching. In addition, 'Camilla Ponticelli' flowers more uniformly and abundantly than its parent, and flowers through the spring and summer. A more detailed comparison of the characteristics of 'Camilla Ponticelli' and 'Italia' are shown in Chart A appearing at the end of the specification.

To the inventor's best knowledge, 'Camilla Ponticelli' is the first variety of *Chrysanthemum frutescens* in Europe to be specifically and purposely selected for the pot growing industry. All other known varieties are cut flower varieties, and only temporarily pot grown.

The accompanying photographic drawing shows in front perspective view typical inflorescence and leaf characteristics of 'Camilla Ponticelli', with the colors being as nearly true as possible with illustrations of this type.

In the following description color references are made to The Royal Horticultural Society Colour Chart. The color values were taken at Sanremo, Italy.

Classification:

*Botanical.*—*Dendranthema Futescens* cv 'Camilla Ponticelli'.

*Commercial.*—Daisy pot mum (greenhouse and outdoor culture).

INFLORESCENCE

Form: Conical.

Type: Single.

Flower head: Single type. Very small diameter (less than 4 cm). Number of rows of involucral bracts are five or fewer. Involucre diameter small, (less than 1.5 cm). Flower has no odor. Flowers in Sanremo, Italy, in early to middle March.

Ray florets: Longitudinal axis of majority of ray florets are reflexing; short corolla tube, convex cross-section, keels two in number; outer floret narrow in width (3–6 mm) and short in length (1–2 cm); tip rounded; outer side of majority of ray florets (when the bloom is opening) 155D; color of inner side of florets when faded (in full bloom) 155B; no color rimming; ray florets low in number (less than 20). Upward attitude of outer floret.

Disc: Tubular type; diameter medium (1–2 cm); color before anther dehiscence 153C; length, inclusive of ovary and ripe anthers, is medium; disc color 13B. Few disc florets, (less than 200).

Receptacle: Small in diameter; raised dome.

PLANT

Height: Short (30–50 cm).

Growth habit: Broad.

Stem: Anthocyanin present; color 139D; thick diameter (greater than 9 mm); pubescence absent; medium number of primary lateral shoots (less than 10); short internode length (less than 2 cm); phyllotaxis 2/5.

Peduncle: Relatively thin; peduncle of terminal flower head is long.

Leaf: Narrow in width (less than 5 cm), medium depth of incision B/A (0.7–0.9), short in length (less than 10 cm), fleshy texture, leaf margin is partly serrated, course density of incision at leaf margin, base acute between lateral lobes, margins of sinus diverging between lateral lobes, base asymmetric, leaf apex cuspidate. Length of petiole, short (less than 3 cm); upward angle between stem and leaf. Leaf color is greyish-green, although the closest color value is 137B. Leaf has no pubescence.

Spray pots: Pyramidal in form.

Branching: Excellent.

Character: Medium tolerance to cold and heat; High resistance to disease and pests.

CHART A

COMPARISON OF 'CAMILLA PONTICELLI' AND 'ITALIA'

| CHARACTERISTIC | 'CAMILLA PONTICELLI' | 'ITALIA' |
|---|---|---|
| Ray Florets | | |
| Color | white with yellow disc | white with yellow disc |
| Length (outer floret) | 1–2 cm | 2–3 cm |
| Number | fewer than 20 | 20–22 |
| Attitude (outer floret) | upward | horizontal |
| Total Flower Diameter | less than 4 cm | 4–6 cm |
| Flowering | spring and summer | fall and winter |
| Plant | | |
| Height | short, 30–50 cm | tall, 70–90 cm |
| Growth habit | compact | medium |
| Number of primary lateral shoots | 5–10 | less than 5 |
| Internode length | less than 2 cm | 2–4 cm |
| Leaf | | |
| length | less than 10 cm | 10–15 cm |
| width | less than 5 cm | 5–10 cm |
| color | grey-green | spinach green |
| attitude with stem | upward | horizontal |
| spray pot culture | yes | no |

Comparisons based on plant material grown at Sanremo, Italy.

I claim:

1. A new and distinct cultivar of *Chrysanthemum frutescens* plant named 'Camilla Ponticelli', as described and illustrated.

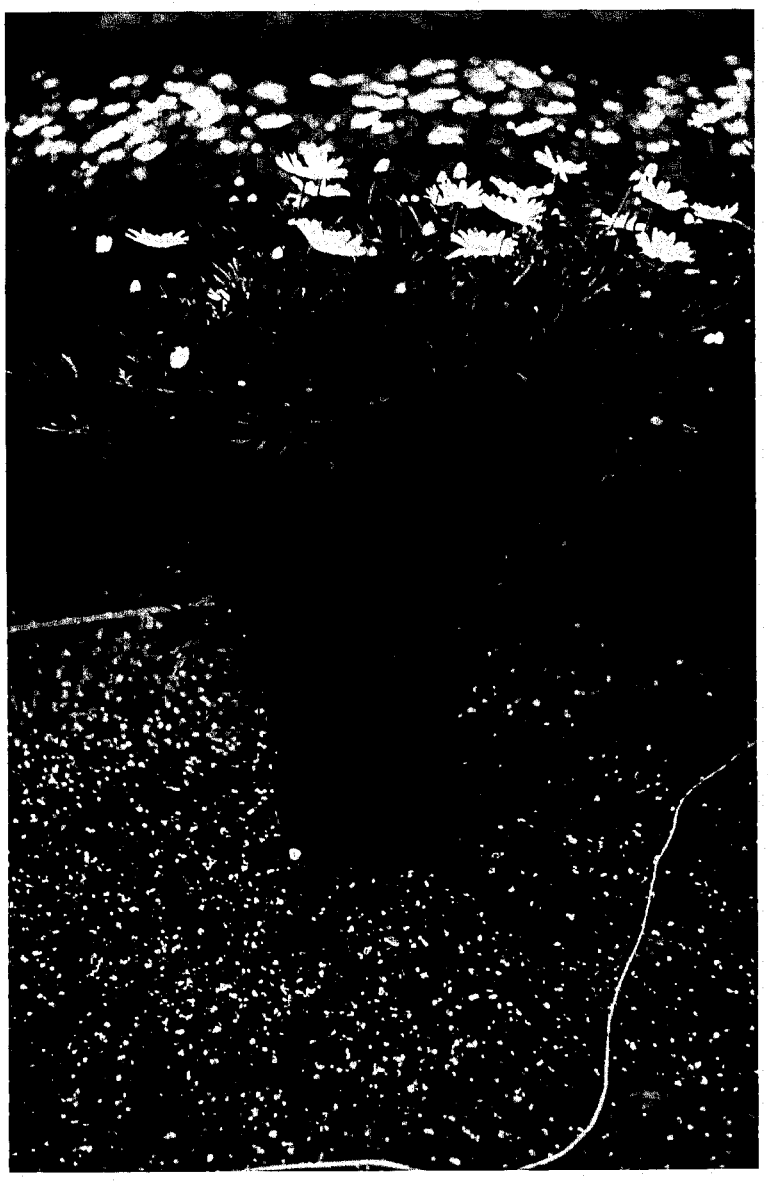

* * * * *